US00PP36367P2

(12) United States Plant Patent
Fell

(10) Patent No.: US PP36,367 P2
(45) Date of Patent: Dec. 31, 2024

(54) ***PORTULACA* PLANT NAMED 'Fantastic'**

(50) Latin Name: *Portulaca umbracticola*
Varietal Denomination: Fantastic

(71) Applicant: David Fell, Waimanalo, HI (US)

(72) Inventor: David Fell, Waimanalo, HI (US)

(73) Assignee: FANTASTIC GARDENS HAWAII, INC., Waimanalo, HI (US)

( * ) Notice: Subject to any disclaimer, the term of this patent is extended or adjusted under 35 U.S.C. 154(b) by 0 days.

(21) Appl. No.: 18/371,431

(22) Filed: Sep. 21, 2023

(51) Int. Cl.
*A01H 5/02* (2018.01)
*A01H 6/30* (2018.01)

(52) U.S. Cl.
USPC ..... Plt./471
CPC ..... *A01H 6/30* (2018.05)

(58) Field of Classification Search
USPC ..... Plt./471
CPC ..... A01H 6/30; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Portulaca* plant named 'Fantastic', characterized by its outwardly spreading to mounding and decumbent plant habit; moderately vigorous to vigorous growth habit and rapid growth rate; freely branching habit; dense and bushy appearance; green and white-colored variegated foliage that is occasionally tinged with reddish purple; freely flowering habit; long flowering period; relatively large orangish to purplish red-colored flowers; and excellent container and garden performance.

2 Drawing Sheets

Figure 1:
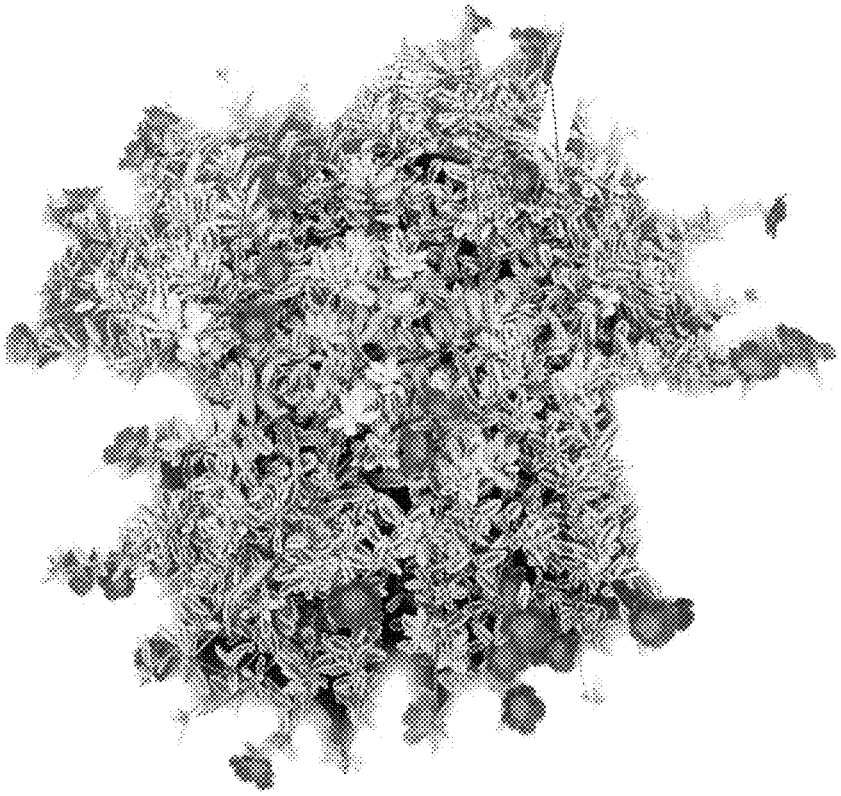

Botanical designation: *Portulaca umbracticola.*
Cultivar denomination: 'FANTASTIC'.

BACKGROUND OF THE INVENTION

The present invention relates to a new and distinct cultivar of *Portulaca* plant, botanically known as *Portulaca umbracticola* and hereinafter referred to by the name 'Fantastic'.

The new *Portulaca* plant is a naturally-occurring branch mutation of an unnamed selection of *Portulaca umbracticola*, not patented. The new *Portulaca* plant was discovered and selected by the Inventor on a single plant of the mutation parent in a controlled environment in Bangkok, Thailand on Dec. 4, 2022.

Asexual reproduction of the new *Portulaca* plant by vegetative terminal cuttings in a controlled greenhouse environment in Waimanalo, Hawaii since Dec. 12, 2022, has shown that the unique features of this new *Portulaca* plant are stable and reproduced true to type in successive generations.

SUMMARY OF THE INVENTION

Plants of the new *Portulaca* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Fantastic'. These characteristics in combination distinguish 'Fantastic' as a new and distinct *Portulaca* plant:

1. Outwardly spreading to mounding and decumbent plant habit.
2. Moderately vigorous to vigorous growth habit and rapid growth rate.

3. Freely branching habit; dense and bushy appearance.
4. Green and white-colored variegated foliage that is occasionally tinged with reddish purple.
5. Freely flowering habit.
6. Long flowering period.
7. Relatively large orangish to purplish red-colored flowers.
8. Excellent container and garden performance.

Plants of the new *Portulaca* can be compared to plants of the unnamed mutation parent selection. Plants of the new *Portulaca* differ primarily from plants of the unnamed mutation parent in the following characteristics:

1. Plants of the new *Portulaca* are slightly slower growing than plants of the mutation parent selection.
2. Leaves of plants of the new *Portulaca* are green and white variegated whereas leaves of plants of the mutation parent selection are solid green in color.

Plants of the new *Portulaca* can be compared to plants of *Portulaca umbraticola* 'DPAZ15', disclosed in U.S. Plant Patent No. 23,243. Plants of the new *Portulaca* differ primarily from plants of 'DPAZ15' in the following characteristics:

1. Leaves of plants of the new *Portulaca* are green and white variegated whereas leaves of plants of 'DPAZ15' are solid green.
2. Flowers of plants of the new *Portulaca* are more red in color than flowers of plants of 'DPAZ15'.

BRIEF DESCRIPTION OF THE PHOTOGRAPHS

The accompanying colored photographs illustrate the overall appearance of the new *Portulaca* plant showing the colors as true as it is reasonably possible to obtain in colored reproductions of this type. Colors in the photographs may differ slightly from the color values cited in the detailed botanical description which accurately describe the colors of the new *Portulaca* plant.

The photograph on the first sheet (FIG. 1) is a top perspective view of a typical flowering plant of 'Fantastic' grown in a container.

Figure 2:
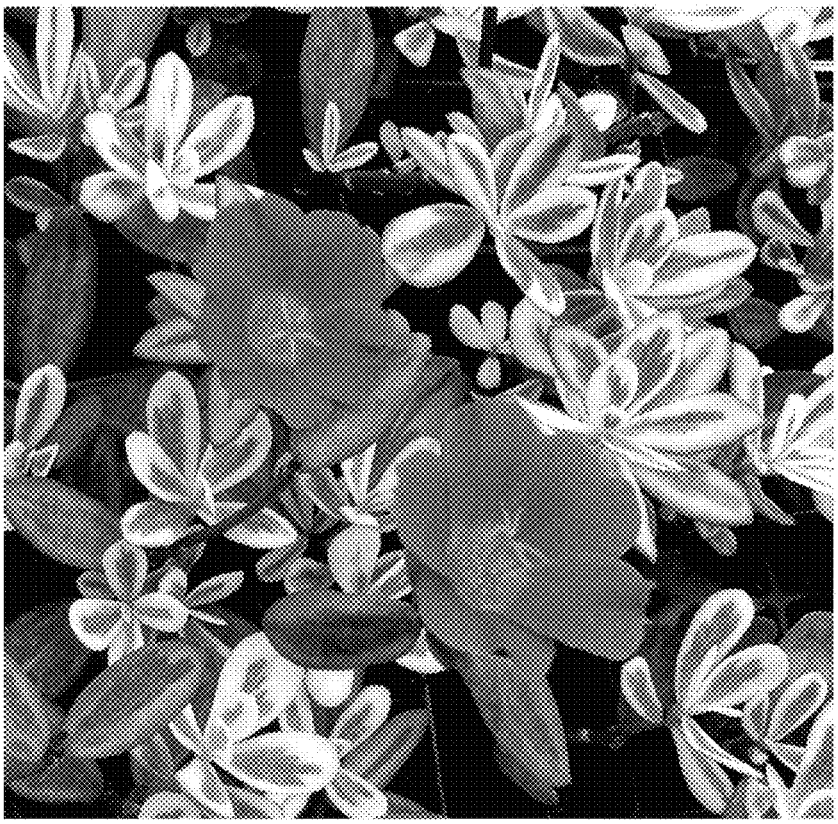

The photograph on the second sheet (FIG. 2) is a close-up view of a typical flowering plant of 'Fantastic'.

DETAILED BOTANICAL DESCRIPTION.

The aforementioned photographs and following observations and measurements describe plants grown during the winter and spring in containers in a shadehouse in Waimanalo, Hawaii and under cultural practices typical of commercial *Portulaca* production. During the production of the plants, day temperatures ranged from 21° C. to 30° C., night temperatures ranged from 14° C. to 21° C. and light levels about 9,000 foot-candles. Plants were about three months old when the photographs were taken and about five to six months old when the description was taken. In the following description, color references are made to The Royal Horticultural Society Colour Chart, 2015 Edition, except where general terms of ordinary dictionary significance are used.

Botanical classification: *Portulaca umbracticola* 'Fantastic'.

Parentage: Naturally-occurring branch mutation of an unnamed selection of *Portulaca umbracticola*, not patented.

Propagation:

*Type*.—By vegetative terminal cuttings.

*Time to initiate roots, summer*.—About four days at temperatures about 28° C.

*Time to initiate roots, winter*.—About six days temperatures about 25° C.

*Time to produce a rooted young plant, summer*.—About ten days at temperatures about 28° C.

*Time to produce a rooted young plant, winter*.—About two weeks at temperatures about 25° C.

*Root description*.—Fine, fibrous; typically white in color, actual color of the roots is dependent on substrate composition, water quality, fertilizers, substrate temperature and age of roots.

*Rooting habit*.—Freely branching; medium density.

Plant description:

*Plant and growth habit*.—Outwardly spreading to mounding and decumbent plant habit; moderately vigorous to vigorous growth habit and rapid growth rate.

*Branching habit*.—Freely branching habit with lateral branches developing potentially at every node; pinching enhances branching potential.

*Plant height*.—About 11 cm to 17 cm.

*Plant diameter* (*area of spread*).—About 22 cm to 26 cm.

Lateral branch/peduncle description:

*Length*.—About 12 cm to 15 cm.

*Diameter*.—About 4 mm to 5 mm.

*Internode length*.—About 1.5 cm.

*Strength*.—Moderately strong; very flexible.

*Texture and luster*.—Smooth, glabrous; moderately glossy to glossy.

*Color, developing and developed*.—Close to 61A.

Leaf description:

*Arrangement*.—Alternate, simple; sessile.

*Length*.—About 2 cm to 2.5 cm.

*Width*.—About 7.5 mm to 12.5 mm.

*Shape*.—Obovate to oblong.

*Apex*.—Cuneate with cuspidate tendencies.

*Base*.—Cuneate.

*Margin*.—Entire.

*Texture and luster, upper surface*.—Smooth, glabrous; fleshy, succulent; slightly glossy.

*Texture and luster, lower surface*.—Smooth, glabrous; fleshy, succulent; matte.

*Venation pattern*.—Pinnate.

*Color*.—Developing and fully expanded leaves, upper surface: Centers, close to 137A surrounded by close to NN155C; margins and marginal edges may be variably tinged with close to 59A to 59B. Developing and fully expanded leaves, lower surface: Centers, close to 137B and 139B surrounded by close to NN155C; margins and marginal edges may be variably tinged with close to 59A to 59B.

Flower description:

*Flower arrangement*.—Single rotate and slightly cupped flowers; freely flowering habit with three to four developing flower buds per terminal with typically one to two open flowers; flowers continuously developing per plant during the flowering season; flowers face mostly upright to outwardly; flowers sessile.

*Fragrance*.—None detected.

*Natural flowering season*.—Plants begin flowering about eight weeks after planting; in the garden, plants flower continuously year-round in Hawaii.

*Flower longevity*.—Dependent on temperature, flowers last one day on the plant; flowers persistent.

*Flower buds*.—Length: About 7.5 mm. Diameter: About 4 mm. Shape: Ovoid. Texture and luster: Smooth, glabrous; somewhat glossy. Color, developing sepals: Close to 137A.

*Flower diameter*.—Large, about 3 cm to 3.25 cm.

*Flower length* (*height*).—About 1.3 cm to 1.6 cm.

*Petals*.—Quantity per flower: Corolla consists of five petals in a single whorl. Length: About 1.75 cm to 2.2 cm. Width: About 1.5 cm to 1.75 cm. Shape: Obovate. Apex: Cuspidate. Base: Cuneate. Margin: Entire, slightly undulate. Texture and luster, upper surface: Smooth, glabrous, satiny; slightly glossy. Texture and luster, lower surface: Smooth, glabrous; matte. Color: When opening and fully opened, upper surface: Close to 54A variably tinged with close to 48A; towards the base, close to 6A; venation, similar to lamina colors. When opening and fully opened, lower surface: Close to between 55B and 54C variably tinged with close to 48B to 48C.

*Sepals*.—Quantity per flower and arrangement: Five in a single whorl; fused at the base. Length: About 5 mm. Width: About 4 mm. Shape: Deltoid. Apex: Acute. Margin: Entire. Texture and luster, upper surface: Smooth, glabrous; glossy. Texture and luster, lower surface: Smooth, glabrous; semi-glossy. Color, upper surface: Close to 144A. Color, lower surface: Close to 137A.

*Reproductive organs*.—Androecium: Quantity of stamens per flower: About 22 to 25. Filament length: About 0.5 mm. Filament color: Close to 4D. Anther shape: Oblong. Anther length: About 1 mm. Anther color: Close to 9A. Amount of pollen: None observed.

*Gynoecium*.—Pistil length: About 2 mm to 2.5 mm. Style length: About 1.75 mm to 2 mm. Style color: Close to 10A. Stigma diameter: About 1 mm. Stigma color: Close to 10A. Ovary color: Close to 144A.

*Fruits and seeds*.—To date, fruit and seed development have not been observed on plants of the new *Portulaca*.

Garden performance:

Plants of the new *Portulaca* have been observed to have excellent garden performance and to tolerate temperatures ranging from about 4.4° C. to about 40.5° C.

Pathogen & pest resistance: To date, plants of the new *Portulaca* have not been shown to be resistant to pathogens and pests common to *Portulaca* plants.

It is claimed:

1. A new and distinct *Portulaca* plant named 'Fantastic' as illustrated and described.

* * * * *